(12) United States Patent
Erden

(10) Patent No.: US 11,580,413 B2
(45) Date of Patent: Feb. 14, 2023

(54) RECOVERING TIMING INFORMATION FROM DNA ENCODED DATA

(71) Applicant: SEAGATE TECHNOLOGY LLC, Cupertino, CA (US)

(72) Inventor: Mehmet Fatih Erden, St. Louis Park, MN (US)

(73) Assignee: SEAGATE TECHNOLOGY LLC, Fremont, CA (US)

( * ) Notice: Subject to any disclaimer, the term of this patent is extended or adjusted under 35 U.S.C. 154(b) by 990 days.

(21) Appl. No.: 16/117,432

(22) Filed: Aug. 30, 2018

(65) Prior Publication Data

US 2019/0130280 A1 May 2, 2019

Related U.S. Application Data

(60) Provisional application No. 62/553,530, filed on Sep. 1, 2017.

(51) Int. Cl.
| | |
|---|---|
| *G06N 3/12* | (2006.01) |
| *G16B 50/30* | (2019.01) |
| *G06V 40/10* | (2022.01) |
| *G06N 3/123* | (2023.01) |

(52) U.S. Cl.
CPC ............. *G06N 3/123* (2013.01); *G06V 40/10* (2022.01); *G16B 50/30* (2019.02)

(58) Field of Classification Search
None
See application file for complete search history.

(56) References Cited

U.S. PATENT DOCUMENTS

| 5,056,121 A | 10/1991 | Ohta et al. |
| 2011/0284762 A1 | 11/2011 | Balakin |
| 2018/0173844 A1 | 6/2018 | Fernandez-Gomez |

OTHER PUBLICATIONS

Wikipedia.com, "Phase-locked loop," 16 pages, dowloaded Jul. 30, 2021 from https://en.wikipedia.org/wiki/Phase-locked_loop.*
Roquet, Nathaniel, et al. "Synthetic recombinase-based state machines in living cells." Science 353.6297 (2016).*

* cited by examiner

*Primary Examiner* — G Steven Vanni
(74) *Attorney, Agent, or Firm* — Holzer Patel Drennan

(57) ABSTRACT

Systems and methods for timing recovery in DNA storage systems is described. In one embodiment, the present systems and methods include generating a unique pattern of DNA bases and use the unique pattern for a phase-locked loop (PLL) field of a data layout, generating a multidimensional mapping, configuring the multidimensional mapping to include one or more prohibited sequences of DNA bases, identifying a prohibited sequence from the multidimensional mapping and use the prohibited sequence for one or more synch-mark (SM) fields of the data layout, prohibiting a User Data field from using any of the prohibited sequences of DNA bases when converting binary data to DNA bases, identifying random insertion and/or deletion of DNA bases in the User Data field, and repairing the random insertion and/or deletion of DNA bases in the User Data field.

18 Claims, 11 Drawing Sheets

Specification includes a Sequence Listing.

SEQUENCE LISTING

```
<160> NUMBER OF SEQ ID NOS: 3

<210> SEQ ID NO 1
<211> LENGTH: 10
<212> TYPE: DNA
<213> ORGANISM: Escherichia coli

<400> SEQUENCE: 1
acacagtgtg                                                            10

<210> SEQ ID NO 2
<211> LENGTH: 12
<212> TYPE: DNA
<213> ORGANISM: Escherichia coli

<400> SEQUENCE: 2
acagtgacag tg                                                         12

<210> SEQ ID NO 3
<211> LENGTH: 18
<212> TYPE: DNA
<213> ORGANISM: Escherichia coli

<400> SEQUENCE: 3
acagtgacag tgacagtg                                                   18
```

RECOVERING TIMING INFORMATION FROM DNA ENCODED DATA

RELATED APPLICATIONS

This application claims the benefit of the filing date of U.S. Provisional Application No. 62/553,530, filed on 1 Sep. 2017, and entitled TIMING RECOVERY FOR DNA STORAGE, the disclosure of which is incorporated, in its entirety by this reference.

NUCLEOTIDE SEQUENCES

This application incorporates by reference the nucleotide sequences in the ASCII text file titled "55071.0171_ST25.txt," the date of creation of this ASCII text file being Aug. 30, 2018, and the size of the ASCII text file in bytes being 695 bytes, the content of which is incorporated, in its entirety, by this reference. The ASCII text file refers to a 10-character sequence identifier 1 (acacagtgtg), a 12-character sequence identifier 2 (acagtgacagtg), and a 18-character sequence identifier 3 (acagtgacagtgacagtg), where "a" refers to adenine, "g" refers to guanine, "c" refers to cytosine, and "t" refers to thymine.

SUMMARY

The present disclosure is directed to methods and systems for timing recovery in deoxyribonucleic acid (DNA) storage systems. In some embodiments, the present systems and methods may include repairing a random insertion and/or deletion of DNA bases (also referred to as nucleotides) in a sequence of DNA bases.

A storage system for timing recovery in DNA storage systems is described. In one embodiment, the storage system device may include one or more storage mediums, including DNA storage mediums, and one or more hardware processors to perform the operations associated with timing recovery in DNA storage systems. In some embodiments, the one or more hardware processors of the storage system may perform the steps of generating a unique pattern of DNA bases and using the unique pattern for a phase-locked loop (PLL) field of a data layout, identifying a prohibited sequence from a multidimensional mapping criteria and using the prohibited sequence for a synchronization mark or synch-mark (SM) field of the data layout, identifying an unintended insertion of DNA sequences and repairing the unintended insertion, and identifying an unintended deletion of DNA sequences and repairing the unintended deletion.

In one embodiment, a deoxyribonucleic acid (DNA) timing recovery system for recovering timing information from DNA encoded data is also described. In one example, the DNA timing recovery system may include one or more processors to embed a first SM field in a first user data field of an encoded DNA sequence and determine a location of a second SM field in the encoded DNA sequence based at least in part on data from the first SM field. In some cases, DNA timing recovery system and the DNA storage system may be the same system or elements of the same system.

In some cases, the second SM field may be subsequent to the first SM field in the encoded DNA sequence. In some cases, the encoded DNA sequence may include at least one of each of a SM field, a phase locked loop (PLL) field, and a user data field.

In some cases, the one or more processors may be configured to compare an expected location of the second SM field to the determined location of the second SM field.

In some cases, the one or more processors may be configured to identify a deletion of one or more DNA bases from the encoded DNA sequence upon determining the determined location occurs in the encoded DNA sequence before the expected location and replace the one or more deleted DNA bases in the encoded DNA sequence.

In some cases, the one or more processors may be configured to identify an insertion of one or more DNA bases from the encoded DNA sequence upon determining the determined location occurs in the encoded DNA sequence after the expected location and remove the one or more inserted DNA bases from the encoded DNA sequence.

In some cases, the one or more processors may be configured to extract timing information from the encoded DNA sequence upon determining the determined location of the second SM field matches the expected location of the second SM field. In some cases, the timing information may include at least one of a phase and a frequency. In some examples, extracting the timing information may include at least one of applying a phase offset to the phase, applying a frequency offset to the frequency, updating a phase offset, updating a frequency offset, running timing recovery for a second user data field subsequent to running timing recovery for the first user data field based at least in part on the updated phase offset or the updated frequency offset or both, applying the updated phase offset to the phase, applying the updated frequency offset to the frequency, or any combination thereof.

In some cases, the SM field may include two different DNA bases repeated one or more times in a sequence of DNA bases. In some cases, the two different DNA bases may include at least one of GT, GC, GA, TG, TC, TA, CG, CT, CA, AG, AT, or AC, where G is a guanine DNA base, T is a thymine DNA base, C is a cytosine DNA base, and A is an adenine DNA base.

In some examples, the PLL field may include DNA bases repeated in a sequence of DNA bases, the repeated DNA bases including at least one of AG, AAGG, or AAAGGG when homopolymers are allowed, or at least one of ACGT, ATGC, and ACAGTG when homopolymers are not allowed.

In some cases, the encoded DNA sequence may include a sequence of DNA bases encoded with data (e.g., user data field). In some examples, the SM field may be configured to include at least one less DNA base than either the PLL field or the user data field. In some embodiments, no two adjacent DNA bases that occur in the SM field may occur adjacently in either the PLL field or the user data field.

A method for timing recovery in DNA storage systems is also described. In one embodiment, the method may include generating a unique pattern of DNA bases and using the unique pattern for a PLL field of a data layout, identifying a prohibited sequence from a multidimensional mapping criteria and using the prohibited sequence for a SM field of the data layout, identifying an unintended insertion of DNA sequences and repairing the unintended insertion, and identifying an unintended deletion of DNA sequences and repairing the unintended deletion.

A method for recovering timing information from deoxyribonucleic acid (DNA) encoded data is also described. In one embodiment, the method may include embedding a first synchronization mark (SM) field in a first user data field of an encoded DNA sequence and determining a location of a second SM field in the encoded DNA sequence based at least in part on data from the first SM field. In some cases, the second SM field may be subsequent to the first SM field in the encoded DNA sequence. In some examples, the encoded DNA sequence may include at least one of each of a synchronization mark (SM) field, a phase locked loop (PLL) field, and a user data field. In some embodiments, the method for timing recovery in DNA storage systems and the method for recovering timing information from DNA encoded data are the same method or elements of the same method.

A computer-program product for recovering timing information from deoxyribonucleic acid (DNA) encoded data is also described. In one embodiment, the computer-program product may include a non-transitory computer-readable medium storing instructions thereon. In some cases, the instructions may be executable by one or more processors to perform the steps of embedding a first synchronization mark (SM) field in a first user data field of an encoded DNA sequence and determining a location of a second SM field in the encoded DNA sequence based at least in part on data from the first SM field. In one example, the second SM field may be subsequent to the first SM field in the encoded DNA sequence. In some cases, the encoded DNA sequence may include at least one of each of a synchronization mark (SM) field, a phase locked loop (PLL) field, and a user data field. In some embodiments, the SM field may be configured to include at least one less DNA base than either the PLL field or the user data field.

An apparatus for timing recovery in DNA storage systems is also described. In one embodiment, the apparatus may include a processor, memory in electronic communication with the processor, and instructions stored in the memory, the instructions being executable by the processor to perform the steps of generating a unique pattern of DNA bases and using the unique pattern for a PLL field of a data layout, identifying a prohibited sequence from a multidimensional mapping criteria and using the prohibited sequence for a SM field of the data layout, identifying an unintended insertion of DNA sequences and repairing the unintended insertion, and identifying an unintended deletion of DNA sequences and repairing the unintended deletion.

The foregoing has outlined rather broadly the features and technical advantages of examples according to this disclosure so that the following detailed description may be better understood. Additional features and advantages will be described below. The conception and specific examples disclosed may be readily utilized as a basis for modifying or designing other structures for carrying out the same purposes of the present disclosure. Such equivalent constructions do not depart from the scope of the appended claims. Characteristics of the concepts disclosed herein, including their organization and method of operation, together with associated advantages will be better understood from the following description when considered in connection with the accompanying figures. Each of the figures is provided for the purpose of illustration and description only, and not as a definition of the limits of the claims.

BRIEF DESCRIPTION OF THE DRAWINGS

A further understanding of the nature and advantages of the present disclosure may be realized by reference to the following drawings. In the appended figures, similar components or features may have the same reference label. Further, various components of the same type may be distinguished by following a first reference label with a dash and a second label that may distinguish among the similar components. However, features discussed for various components, including those having a dash and a second reference label, apply to other similar components. If only the first reference label is used in the specification, the description is applicable to any one of the similar components having the same first reference label irrespective of the second reference label.

DETAILED DESCRIPTION

Figure 1:
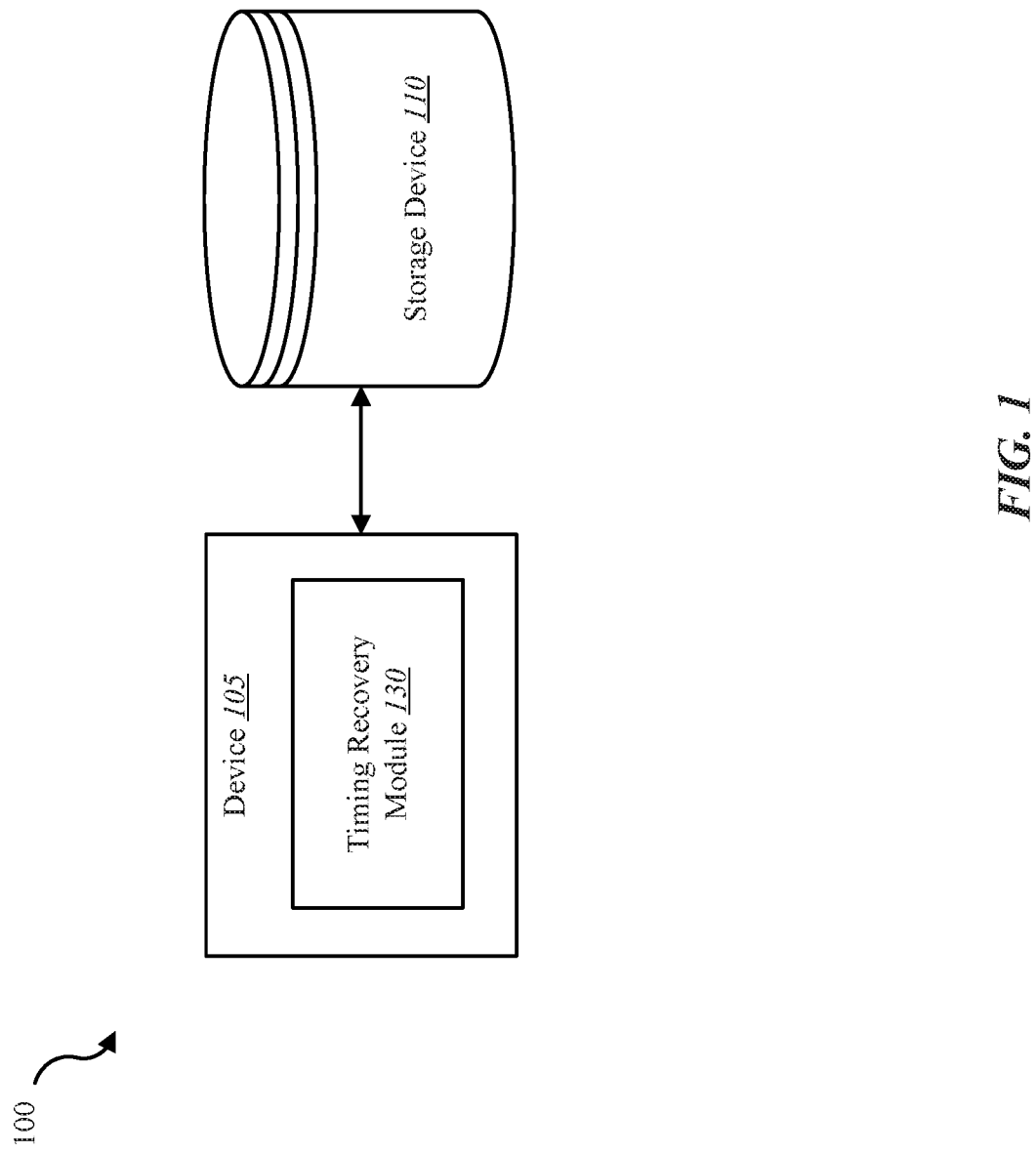
FIG. 1 is a block diagram of an example of a system in accordance with various embodiments.

The following relates generally to timing recovery for DNA storage systems. In one embodiment, the present systems and methods enable DNA storage specific timing recovery. Specifically, the present systems and methods may be configured to define DNA storage specific Phase-Locked Loop (PLL) and Synch Mark (SM) patterns to acquire timing information in a relatively quick and accurate manner. The present systems and methods may be configured to detect and correct any insertions and/or deletions within DNA sequencing. In some cases, a data layout of the present systems and methods may enable the detection and/or correction of insertions and/or deletions in DNA sequencing.

The demand for data storage is increasing exponentially. As a result, alternative storage methods are attracting more and more attention. Because of its relatively high storage density potential, deoxyribonucleic acid (DNA) storage is one alternative storage method attracting attention. In one example, a storage density greater than $10^{21}$ bits/cm3 may be achieved when individual DNA molecules are used to store binary bits of user data, a significantly higher storage density than is currently available.

One or more read processes for DNA storage currently exist. In some cases, a DNA write process includes converting a sequence of binary data to a sequence of DNA bases. In some embodiments, a DNA read process includes converting a sequence of DNA bases to a sequence of binary data. In one example, a DNA molecule may include the four nucleic acids or DNA bases (also referred to as DNA nucleotides) Adenine (A), Guanine (G), Cytosine (C), and Thymine (T). In this example, a DNA strand may pass through a nanopore of a lipid membrane. As the DNA strand passes through the nanopore, the bases of the DNA sequence may at least partially block an ionic current that flows through the nanopore. Changes in the ionic current may result from different bases passing through the nanopore. In one embodiment, the present systems and methods may be based at least in part on a DNA read process. In one non-limiting example, the read process may be configured where Adenine (A) may yield the highest current output, followed by Cytosine (C), then Thymine (T), and finally Guanine (G). In one embodiment, the read process may be configured where a DNA base other than Guanine yields the lowest current output, a DNA base other than Thymine yields the next highest current output, a DNA base other than Cytosine yields the next highest current output, and a DNA base other than Adenine yields the highest current output.

Timing information is a key aspect within communication theory. Timing information is a relatively important part in detecting and extracting the user information encoded in DNA molecules. The present systems and methods describe DNA storage specific Phase-Locked Loop (PLL) and Synch Mark (SM) patterns followed by PLL to acquire timing information in a relatively quick and accurate manner. In one embodiment, a data layout of the present systems and methods may enable detection and/or correction of insertions and/or deletions of DNA bases within a particular DNA sequence.

FIG. 1 is a block diagram illustrating one embodiment of an environment 100 in which the present systems and methods may be implemented. The environment may include device 105 and storage device 110. The storage device 110 may include any combination of DNA storage systems, hard disk drives, solid state drives, and/or hybrid drives that include a DNA storage system, as well as a hard disk drive and/or a solid state drive. In some embodiments, the systems and methods described herein may be performed on a single device such as device 105. In some cases, the methods described herein may be performed on multiple storage devices or a network of storage devices. Examples of device 105 include a storage server, a storage enclosure, a storage controller, storage drives in a distributed storage system, storage drives on a cloud storage system, storage devices on personal computing devices, storage devices on mobile computing devices, storage devices on a server, or any combination thereof. In some configurations, device 105 may include timing recovery module 130. In one example, the device 105 may be coupled to storage device 110. In some embodiments, device 105 may be a component of a host of the storage device 110 such as an operating system, host hardware system, or any combination thereof.

In one embodiment, device 105 may include one or more computing devices that each includes one or more processors, memory, and/or one or more storage devices. In some cases, device 105 may include a wireless storage device. In some embodiments, device 105 may include a cloud drive for a home or office setting. In one embodiment, device 105 may include a network device such as a switch, router, access point, or any combination thereof. In one example, device 105 may be operable to receive data streams, store and/or process data, and/or transmit data from, to, or in conjunction with one or more local and/or remote computing devices.

The device 105 may include a database. In some cases, the database may be internal to device 105. In some embodiments, storage device 110 may include a database. Additionally, or alternatively, the database may include a connection to a wired and/or a wireless database. Additionally, as described in further detail herein, software and/or firmware (for example, stored in memory) may be executed on one or more processors of device 105. Such software and/or firmware executed on the one or more processors may be operable to cause the device 105 to monitor, process, summarize, present, and/or send a signal associated with the operations described herein.

In some embodiments, storage device 110 may connect to device 105 via one or more networks. Examples of networks include cloud networks, local area networks (LAN), wide area networks (WAN), virtual private networks (VPN), a personal area network, near-field communication (NFC), a telecommunications network, wireless networks (using 802.11, for example), and cellular networks (using 3G and/or LTE, for example), or any combination thereof. In some configurations, the network may include the Internet and/or an intranet. The device 105 may receive and/or send signals over a network via a wireless communication link. In some embodiments, a user may access the functions of device 105 via a local computing device, remote computing device, and/or network device. For example, in some embodiments, device 105 may include an application that interfaces with a user. In some cases, device 105 may include an application that interfaces with one or more functions of a network device, remote computing device, and/or local computing device.

In one embodiment, the storage device 110 may be internal to device 105. As one example, device 105 may include a storage controller that interfaces with storage media of storage device 110. In one embodiment, timing recovery module 130 may enable timing recovery in a DNA storage system. In some embodiments, timing recovery module 130 may repair a random insertion and/or deletion of DNA bases in a sequence of DNA bases of the DNA storage system.

In some cases, device 105 may include one or more DNA timing agents configured to recover timing information from a sequence of encoded DNA. The DNA timing agent may include software, firmware, and/or hardware configured to recover timing information from encoded DNA sequences. In one embodiment, a single DNA timing agent may perform each of the operations described herein. Additionally or alternatively, a first DNA timing agent may perform one or more first operations described herein, while a second DNA timing agent may perform one or more second operations described herein, where the one or more second operations are each different than the one or more first operations. In one embodiment, timing recovery module 130 may include one or more DNA timing agents or operate in conjunction with one or more timing agents. In some embodiments, a DNA timing agent may include timing recovery module 130.

Figure 2:
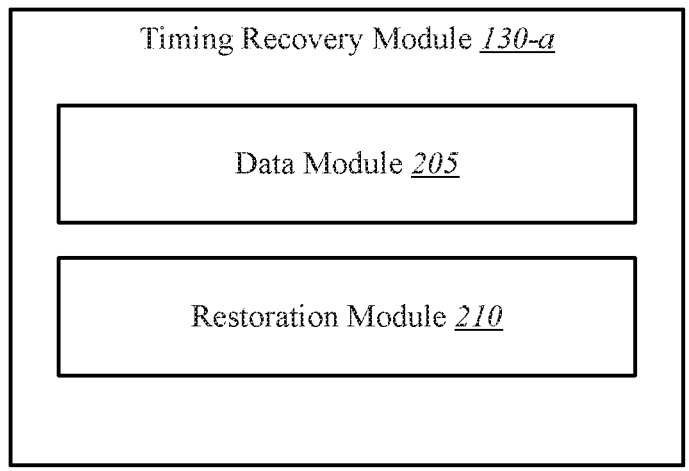
FIG. 2 shows a block diagram of one or more modules in accordance with various aspects of this disclosure.

FIG. 2 shows a block diagram of timing recovery module 130-*a*. The timing recovery module 130-*a* may include one or more processors, memory, and/or one or more storage devices. The timing recovery module 130-*a* may include data module 205 and restoration module 210. The timing recovery module 130-*a* may be one example of timing recovery module 130 of FIG. 1. Each of the illustrated components may be in communication with each other.

In one embodiment, timing recovery module 130-*a* may enable systems and methods to store binary data in sequences of DNA bases. In one embodiment, data module 205 may generate a unique pattern of DNA bases and use the unique pattern for a PLL field of a data layout of the present systems and methods. The data layout may include the PLL field, one or more SM fields, and one or more User Data fields. In some cases, data module 205 may generate a multidimensional mapping between binary data and DNA bases. In one embodiment, the User Data fields may include a sequence of DNA bases. In some cases, the particular order of the sequence of DNA bases in the User Data fields may be based at least in part on the multidimensional mapping between binary data and DNA bases generated by data module 205. For example, data module 205 may identify a particular string of binary data (e.g., 0100100011001011110) and convert the particular string of binary data into a particular sequence of DNA bases according to the multidimensional mapping.

In some examples, data module 205 may configure the multidimensional mapping to include one or more prohibited sequences of DNA bases. In one embodiment, data module 205 may prohibit the User Data field from using any of the prohibited sequences of DNA bases when converting binary data to DNA bases. However, in some cases data module 205 may identify a prohibited sequence from the multidimensional mapping and use the prohibited sequence for one or more SM fields of the data layout. For example, data module 205 may identify a repeating pattern "CTCT . . . " as a prohibited sequence and thus use the repeating pattern "CTCT . . . " as the data in an SM field of the data layout.

In some examples, restoration module 210 may detect an unintended insertion of one or more DNA bases in a sequence of DNA bases. For example, restoration module 210 may detect one or more DNA bases added to a sequence of DNA bases of a User Data field. In one embodiment, restoration module 210 may repair the unintended insertion. In one example, restoration module 210 may identify the particular inserted DNA bases and remove the identified DNA bases from the sequence of DNA bases to which the identified DNA bases were added. Additionally or alternatively, restoration module 210 may detect an unintended deletion of one or more DNA bases from a sequence of DNA bases. For example, restoration module 210 may detect one or more DNA bases deleted from a sequence of DNA bases of a User Data field. In one embodiment, restoration module 210 may repair the unintended deletion. In one example, restoration module 210 may identify the particular deleted DNA bases and add the identified DNA bases back into the sequence of DNA bases to which the identified DNA bases were deleted.

In one embodiment, data module 205 may be configured to embed a first synchronization mark (SM) field in a first user data field of an encoded DNA sequence. In one embodiment, data module 205 may be configured to determine a location of a second SM field in the encoded DNA sequence based at least in part on data from the first SM field. In one example, the second SM field may be subsequent to the first SM field in the encoded DNA sequence. In some cases, the encoded DNA sequence may include at least one of each of a synchronization mark (SM) field, a phase locked loop (PLL) field, and a user data field. In some embodiments, the SM field may be configured to include at least one less DNA base than either the PLL field or the user data field.

In one embodiment, data module 205 may be configured to compare an expected location of the second SM field to the determined location of the second SM field. In one example, restoration module 210 may be configured to identify a deletion of one or more DNA bases from the encoded DNA sequence upon determining the determined location occurs in the encoded DNA sequence before the expected location. In one example, restoration module 210 may be configured to replace the one or more deleted DNA bases in the encoded DNA sequence.

In one example, restoration module 210 may be configured to identify an insertion of one or more DNA bases from the encoded DNA sequence upon determining the determined location occurs in the encoded DNA sequence after the expected location. In one example, restoration module 210 may be configured to remove the one or more inserted DNA bases from the encoded DNA sequence. In one example, data module 205 may be configured to extract timing information from the encoded DNA sequence upon determining the determined location of the second SM field matches the expected location of the second SM field.

In some examples, the timing information may include at least one of a phase and a frequency. In some examples, extracting the timing information may include at least one of applying a phase offset to the phase, applying a frequency offset to the frequency, updating a phase offset, updating a frequency offset, running timing recovery for a second user data field subsequent to running timing recovery for the first user data field based at least in part on the updated phase offset or the updated frequency offset or both, applying the updated phase offset to the phase, applying the updated frequency offset to the frequency, or any combination thereof.

In some examples, the SM field may include two DNA bases repeated in a sequence of DNA bases. In some cases, the two repeated DNA bases may include at least one of GT, GC, GA, TG, TC, TA, CG, CT, CA, AG, AT, or AC, where G is a guanine DNA base, T is a thymine DNA base, C is a cytosine DNA base, and A is an adenine DNA base. For example, the two repeated DNA bases may include GT DNA base pairs, giving a sequence of "GTGTGT . . . " in the SM field, etc. In another example, the two repeated DNA bases may include CA DNA base pairs, giving a sequence of "CACACA . . . " in the SM field, etc.

In some cases, the PLL field may include at least two different DNA bases repeated one or more times in a sequence of DNA bases. In one example, the DNA bases repeated in the PLL field may include at least one of AG, AAGG, or AAAGGG when homopolymers are allowed, or at least one of ACGT, ATGC, and ACAGTG when homopolymers are not allowed. For example, the DNA bases repeated in the PLL may include "AG," giving the sequence "AGAGAG . . . " in the PLL field. In some cases, how many times a segment of DNA bases such as "ACAGTG" may be repeated in the PLL field may be determined by a predetermined threshold. For example, the predetermined threshold may determine that the PLL field can hold up to some predetermined number DNA bases (e.g., a maximum of 20 DNA bases, a maximum of 100 DNA bases, a maximum of 1000 DNA bases, etc.). Accordingly, a given segment such as "AG," "AAGG," "ATGC," "ACAGTG," etc., may be repeated in the PLL field as many times as permitted without the sequence exceeding the predetermined threshold.

In some examples, the encoded DNA sequence may include a sequence of DNA bases encoded with data. In some examples, the SM field may be configured to include at least one less DNA base than either the PLL field or the user data field. In some embodiments, no two adjacent DNA bases that occur in the SM field may occur adjacently in either the PLL field or the user data field.

Figure 3:
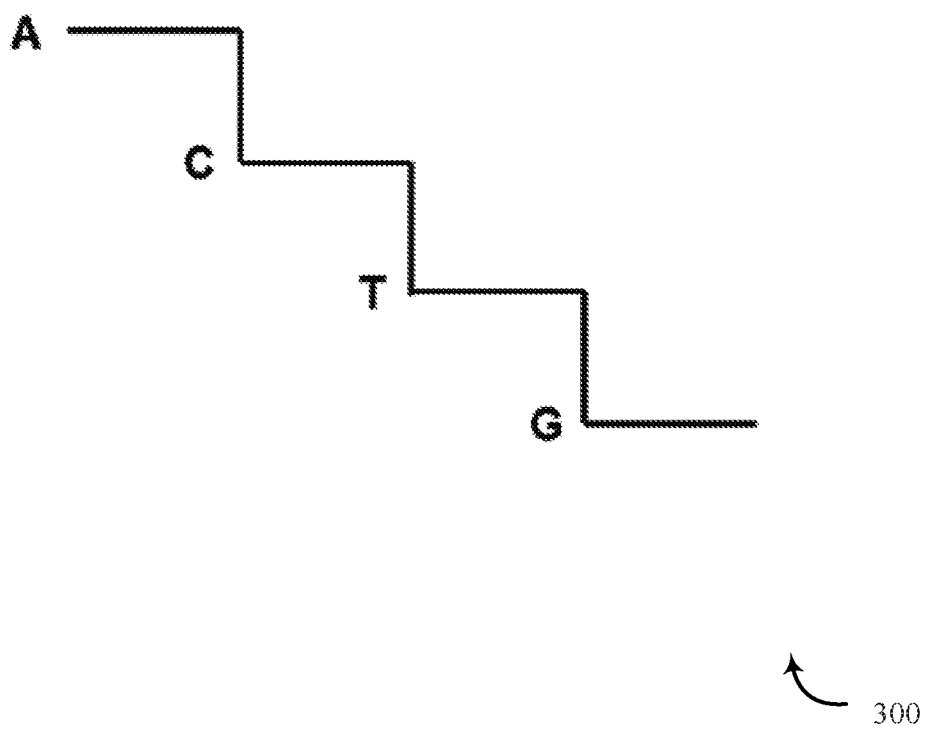
FIG. 3 shows a diagram of signal levels in accordance with various aspects of this disclosure.

FIG. 3 shows a diagram of signal levels 300 in accordance with various aspects of this disclosure. The signal levels 300 may be associated with a multi-dimensional mapping of DNA sequences, in accordance with various examples. In some cases, signal levels 300 may be configured by timing recovery module 130 of FIGS. 1 and/or 2. In one embodiment, signal levels 300 may be configured based at least in part on an ionic current through a nanopore of a lipid membrane. In some cases, signal levels 300 may be referred to as current levels.

As illustrated, timing recovery module 130 may configure a highest current level of the signal levels 300 to be associated with DNA base Adenine (A), a second highest current level of the signal levels 300 to be associated with DNA base Cytosine (C), a third highest current level of the signal levels 300 to be associated with DNA base Thymine (T), and a lowest current level of the signal levels 300 to be associated with DNA base Guanine (G). The illustrated signal levels 300 depict one example of a signal level configuration in relation to a DNA storage system. For example, in some embodiments, the present systems and methods may use a configuration where Cytosine, Thymine, or Guanine is the highest current level; where Adenine, Thymine, or Guanine is the second highest current level; where Adenine, Cytosine, or Guanine is the third highest current level; and/or where Adenine, Cytosine, or Thymine is the lowest current level.

Figure 4:
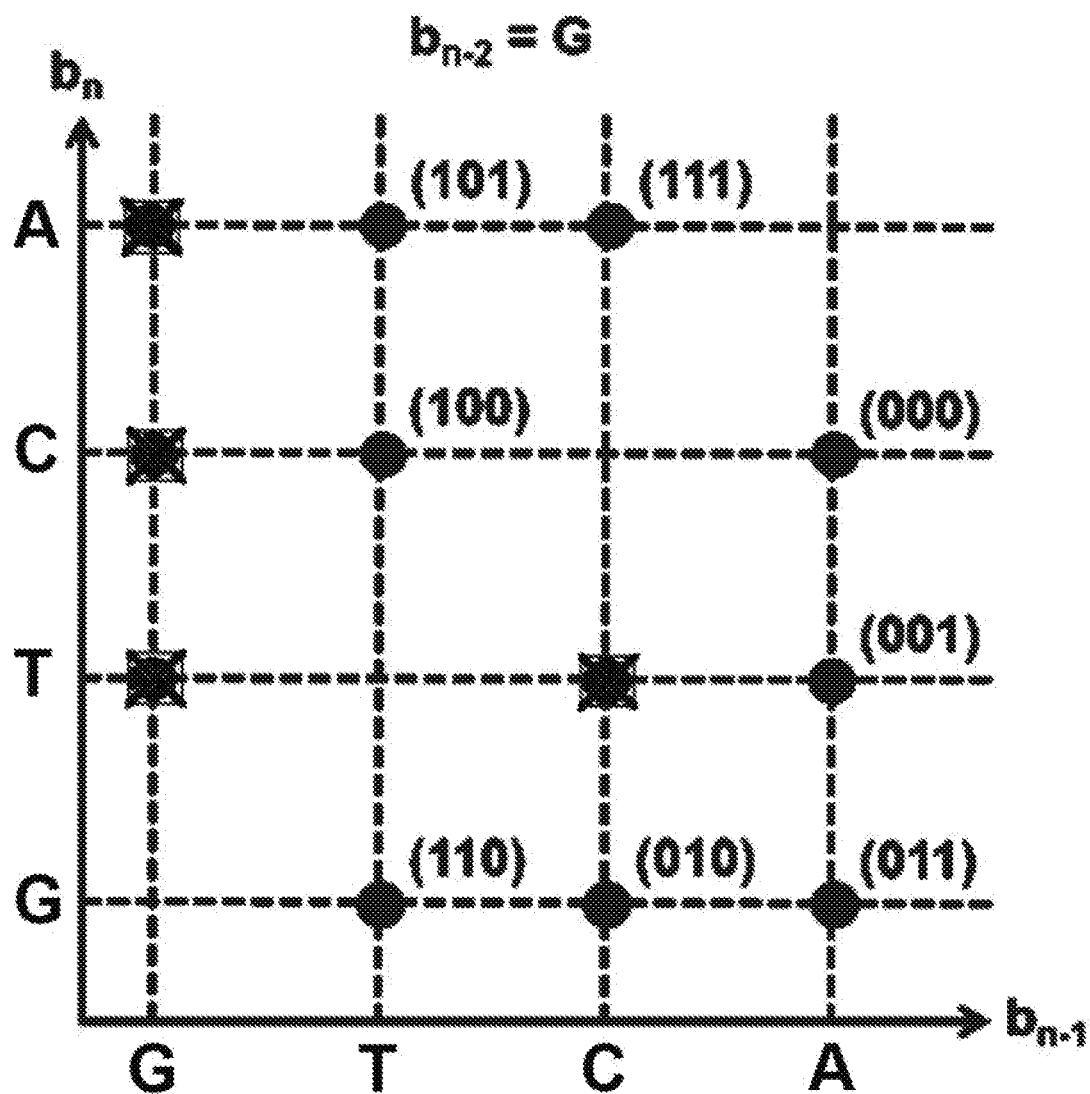
FIG. 4 shows a diagram of a mapping in accordance with various aspects of this disclosure.

FIG. 4 shows a diagram of a mapping 400 in accordance with various aspects of this disclosure. The mapping 400 may be associated with a multi-dimensional mapping of DNA sequences, in accordance with various examples. Mapping 400 may be generated by mapping module 205 of FIG. 2.

As depicted in mapping 400, when $b_{n-2}$=G, timing recovery module 130 may eliminate combinations in mapping 400 with $b_{n-1}$=G to eliminate homopolymers in the DNA encoding, leaving 9 possible combinations. In one embodiment, among the remaining 9 combinations, timing recovery module 130 may eliminate $(b_{n-1}, b_n)$=(C, T) when $b_{n-2}$=G, reducing the maximum number of node neighbors for each node to two neighbors. For instance, before eliminating $(b_{n-1}, b_n)$=(C, T), $(b_{n-1}, b_n)$=(A, T) included three node neighbors: $(b_{n-1}, b_n)$=(A, C), $(b_{n-1}, b_n)$=(A, G), and $(b_{n-1}, b_n)$=(C, T). With $(b_{n-1}, b_n)$=(C, T) eliminated, $(b_{n-1}, b_n)$=(A, T) is left with a maximum of two node neighbors: $(b_{n-1}, b_n)$=(A, C) and $(b_{n-1}, b_n)$=(A, G). In some cases, timing recovery module 130 may assign 3-bit combinations to the remaining 8 pairs $(b_{n-1}, b_n)$ as follows, resulting in a maximum 1-bit difference between the remaining neighboring pairs $(b_{n-1}, b_n)$:

$(b_{n-1}, b_n)$=(A, C) maps to 000
$(b_{n-1}, b_n)$=(A, T) maps to 001
$(b_{n-1}, b_n)$=(A, G) maps to 011
$(b_{n-1}, b_n)$=(C, G) maps to 010
$(b_{n-1}, b_n)$=(T, G) maps to 110
$(b_{n-1}, b_n)$=(T, C) maps to 100
$(b_{n-1}, b_n)$=(T, A) maps to 101
$(b_{n-1}, b_n)$=(C, A) maps to 111

Figure 5:
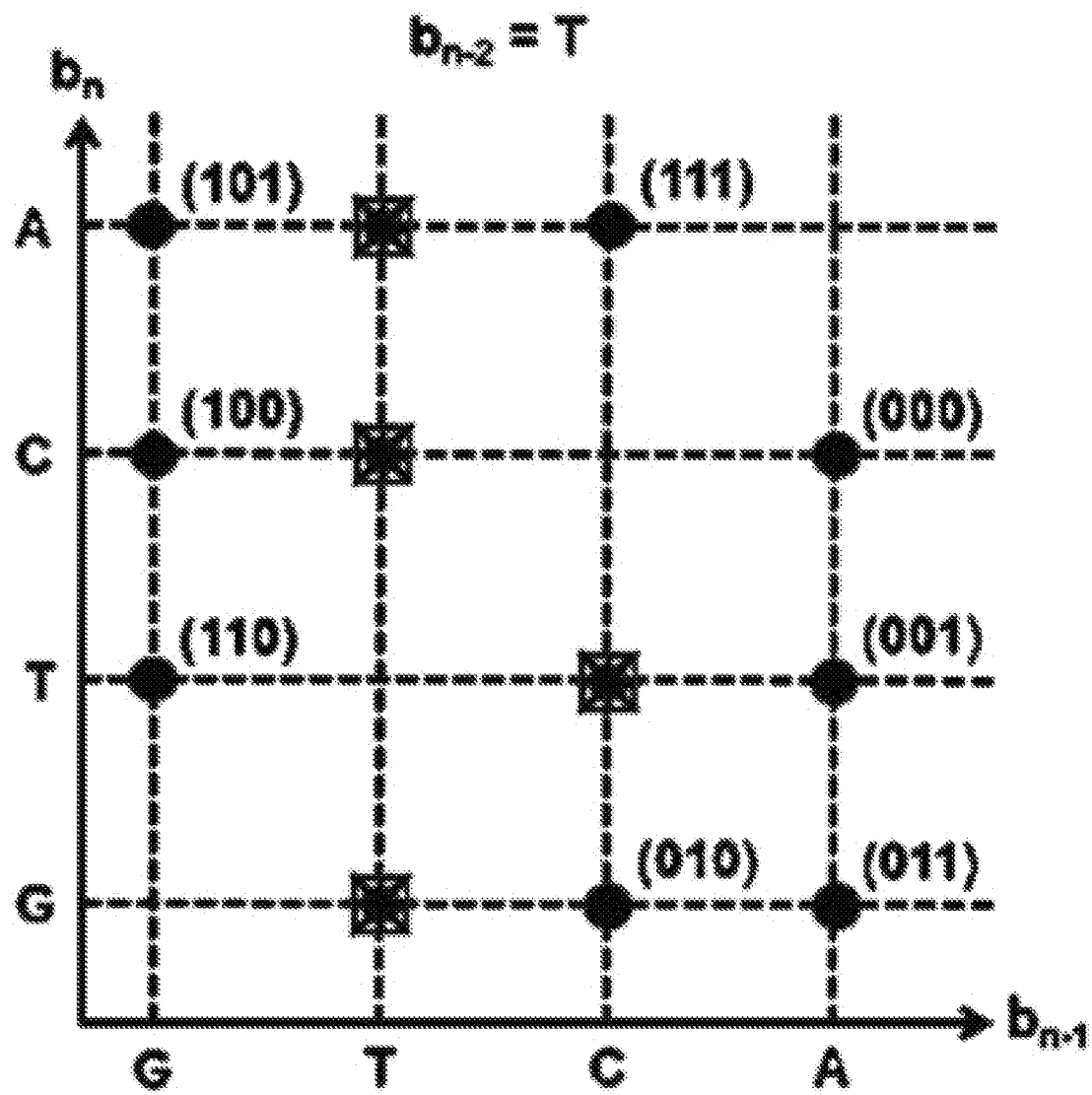
FIG. 5 shows a diagram of a mapping in accordance with various aspects of this disclosure.

FIG. 5 shows a diagram of a mapping 500 in accordance with various aspects of this disclosure. The mapping 500 may be associated with a multi-dimensional mapping of DNA sequences, in accordance with various examples. Mapping 500 may be generated by mapping module 205 of FIG. 2.

As depicted in mapping 500, when $b_{n-2}$=T, timing recovery module 130 may eliminate combinations in mapping 400 of FIG. 4 with $b_{n-1}$=T to eliminate homopolymers in the DNA encoding, leaving 9 possible combinations. Among the remaining 9 combinations, timing recovery module 130 may eliminate $(b_{n-1}, b_n)$=(C, T) when $b_{n-2}$=T, reducing the maximum number of node neighbors for each node to two. In some cases, timing recovery module 130 may assign the 3-bit combinations to the remaining 8 pairs $(b_{n-1}, b_n)$ as follows, resulting in a maximum 1-bit difference between the neighboring pairs $(b_{n-1}, b_n)$:

$(b_{n-1}, b_n)$=(A, C) maps to 000
$(b_{n-1}, b_n)$=(A, T) maps to 001
$(b_{n-1}, b_n)$=(A, G) maps to 011
$(b_{n-1}, b_n)$=(C, G) maps to 010
$(b_{n-1}, b_n)$=(G, T) maps to 110
$(b_{n-1}, b_n)$=(G, C) maps to 100
$(b_{n-1}, b_n)$=(G, A) maps to 101
$(b_{n-1}, b_n)$=(C, A) maps to 111

Figure 6:
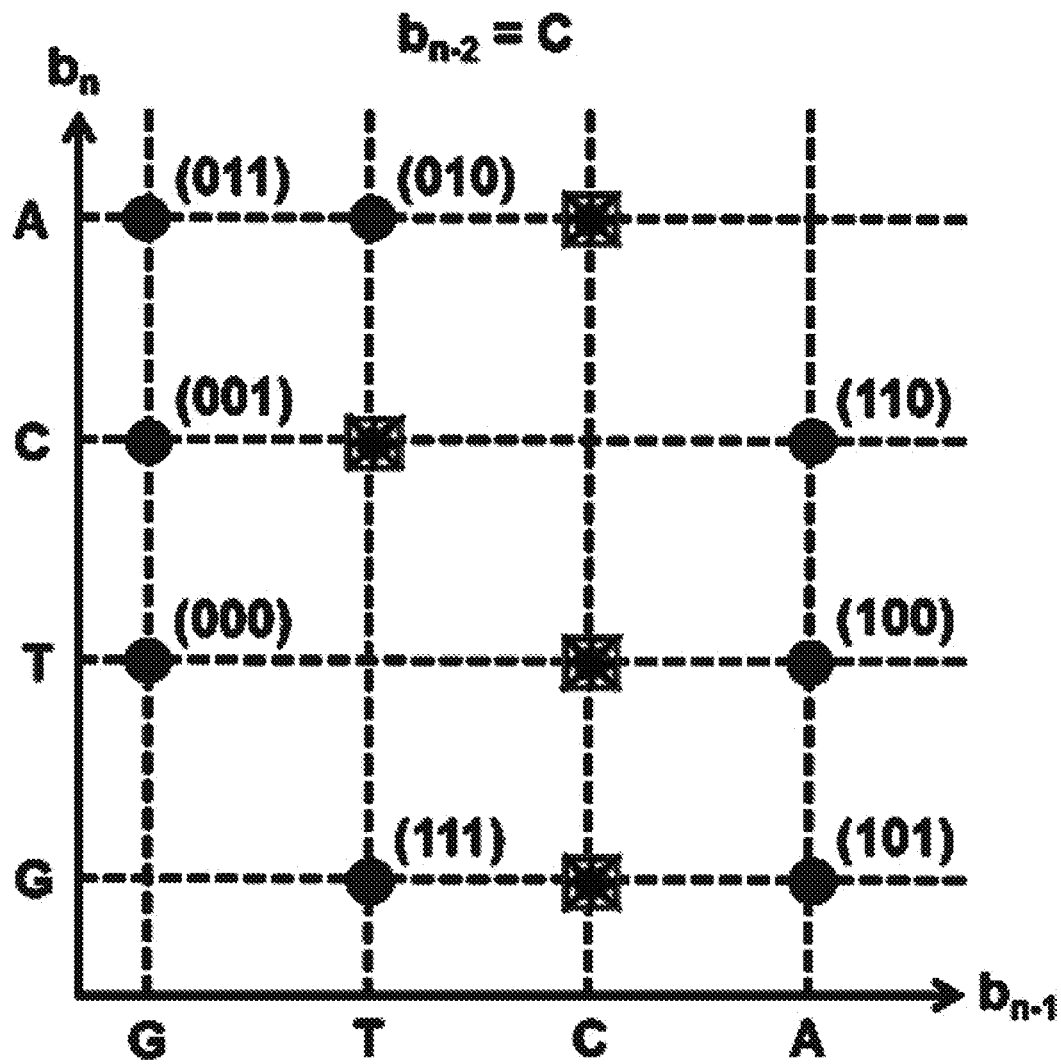
FIG. 6 shows a diagram of a mapping in accordance with various aspects of this disclosure.

FIG. 6 shows a diagram of a mapping 600 in accordance with various aspects of this disclosure. The mapping 600 may be associated with a multi-dimensional mapping of DNA sequences, in accordance with various examples. Mapping 600 may be generated by mapping module 205 of FIG. 2.

As depicted in mapping 600, when $b_{n-2}$=C, timing recovery module 130 may eliminate combinations in mapping 400 of FIG. 4 with $b_{n-1}$=C to eliminate homopolymers in the DNA encoding, leaving 9 possible combinations. Among the remaining 9 combinations, timing recovery module 130 may eliminate $(b_{n-1}, b_n)$=(T, C) when $b_{n-2}$=C, reducing the maximum number of node neighbors for each node to two. In some cases, timing recovery module 130 may assign the 3-bit combinations to the remaining 8 $(b_{n-1}, b_n)$ as follows, resulting in a maximum 1-bit difference between the neighboring pairs $(b_{n-1}, b_n)$:

$(b_{n-1}, b_n)$=(A, C) maps to 110
$(b_{n-1}, b_n)$=(A, T) maps to 100
$(b_{n-1}, b_n)$=(A, G) maps to 101
$(b_{n-1}, b_n)$=(T, G) maps to 111
$(b_{n-1}, b_n)$=(G, T) maps to 000
$(b_{n-1}, b_n)$=(G, C) maps to 001
$(b_{n-1}, b_n)$=(G, A) maps to 011
$(b_{n-1}, b_n)$=(T, A) maps to 010

Figure 7:
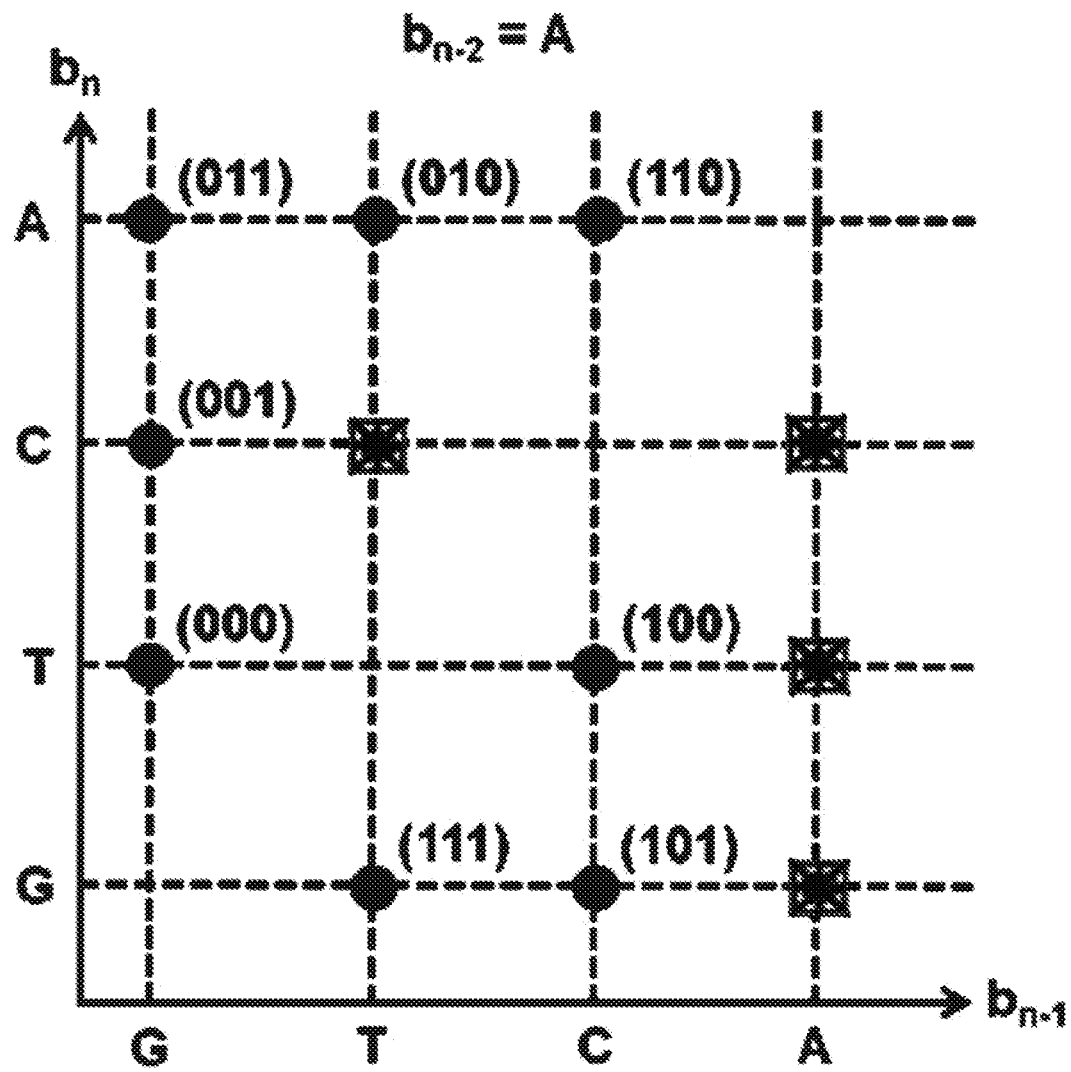
FIG. 7 shows a diagram of a mapping in accordance with various aspects of this disclosure.

FIG. 7 shows a diagram of a mapping 700 in accordance with various aspects of this disclosure. The mapping 700 may be associated with a multi-dimensional mapping of DNA sequences, in accordance with various examples. Mapping 700 may be generated by mapping module 205 of FIG. 2.

As depicted in mapping 700, when $b_{n-2}$=A, timing recovery module 130 may eliminate combinations in mapping 400 of FIG. 4 with $b_{n-1}$=A to eliminate homopolymers in the DNA encoding, leaving 9 possible combinations. Among the remaining 9 combinations, eliminate $(b_{n-1}, b_n)$=(T, C) when $b_{n-2}$=A, reducing the maximum number of node neighbors for each node to two. In some cases, timing recovery module 130 may assign the 3-bit combinations to the remaining 7 pairs $(b_{n-1}, b_n)$ as follows, resulting in a maximum 1-bit difference between the neighboring pairs $(b_{n-1}, b_n)$:

$(b_{n-1}, b_n)$=(C, A) maps to 110
$(b_{n-1}, b_n)$=(C, T) maps to 100
$(b_{n-1}, b_n)$=(C, G) maps to 101
$(b_{n-1}, b_n)$=(T, G) maps to 111
$(b_{n-1}, b_n)$=(G, T) maps to 000
$(b_{n-1}, b_n)$=(G, C) maps to 001
$(b_{n-1}, b_n)$=(G, A) maps to 011
$(b_{n-1}, b_n)$=(T, A) maps to 010

Figure 8:
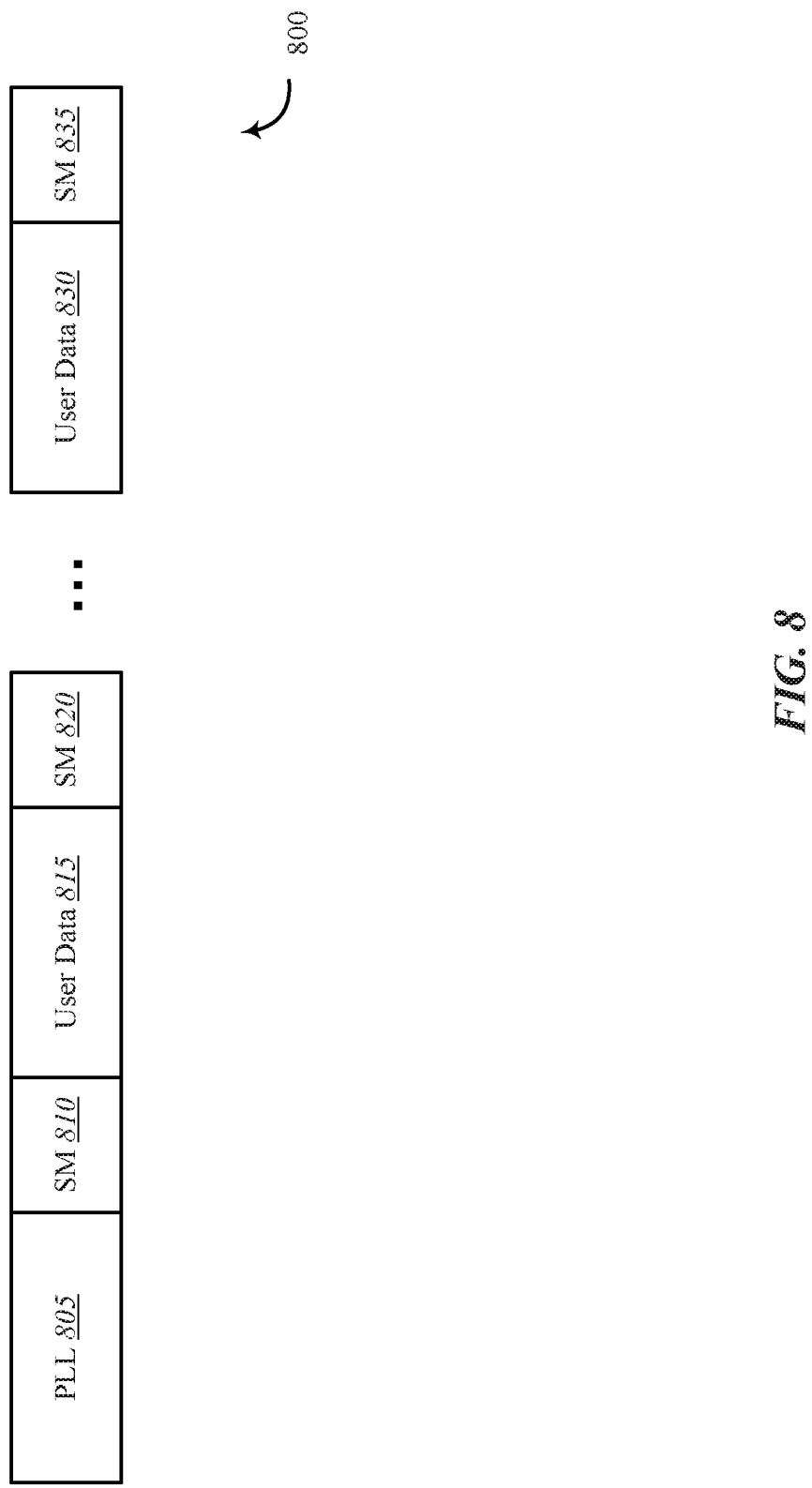
FIG. 8 shows a diagram of a data layout in accordance with various aspects of this disclosure.

FIG. 8 shows a diagram of a data layout 800 in accordance with various aspects of this disclosure. The data layout 800 may be associated with a multi-dimensional mapping of DNA sequences, in accordance with various examples. The data layout 800 may be generated by timing recovery module 130 of FIGS. 1 and/or 2.

As illustrated, data layout 800 may include PLL field 805, SM field 810, User Data field 815, and SM field 820. In some cases, data layout 800 may include one or more additional fields such as User Data field 830 and SM field 835. As shown, data layout 800 may include PLL field 805 followed by one or more SM fields and/or User Data fields. An SM field such as SM field 810 may enable the present systems and methods to confirm accurate acquisition of timing information. In some cases, a User Data field such as User Data field 815 may follow after an SM field. In some cases, each User Data field of data layout 800 may include encoded user information. For example, User Data field 815 may include a sequence of DNA bases generated according to a multidimensional map configured to map a string of binary data to a sequence of DNA bases. In some examples, as shown, the data layout 800 may include one or more SM fields interspersed between User Data fields.

In one embodiment, a PLL field such as PLL field 805 may include a predefined sequence of data. In some cases, PLL field 805 may be used by timing recovery circuitry to acquire the timing information. In some examples, the timing recovery operations of timing recovery module 130 may extract the timing information based at least in part on the transitions within PLL field 805. In one embodiment, PLL field 805 may be configured to have as many transitions as possible between maximally separated signal amplitude levels, as constrained by a predefined length or size of PLL field 805. In some embodiments, the maximally separated signal amplitude levels may be based at least in part on the signal levels shown in FIG. 3. However, the maximally separated signal amplitude levels of PLL field 805 may be configured from any signal level configuration other than that of FIG. 3. In FIG. 3, bases A and G have the maximum signal swing. Accordingly, in one embodiment a DNA base sequence of "AGAGAG . . . " may be used for PLL field 805. However, in some cases the DNA read process circuitry may not have sufficient bandwidth and/or be quick enough to recover the transitions between A and G in the sequence "AGAGAG . . . ." Accordingly, in some cases, longer marks of A and G may be used. For example, a DNA sequence of "AAGGAAGG . . . " may be used for PLL field 805. However, using homopolymers may result in an increase in system error rates. A homopolymer may be a run of identical bases in a DNA sequence such as AA, CC, TT, or GG. In some cases, timing recovery module 130 may implement a constraint that prohibits the use of homopolymers. As a result, a DNA sequence with homopolymers such as "AAGGAAGG . . . " may be prohibited. Thus, in some cases timing recovery module 130 may use a DNA sequence such as "ACAGTGACAGTG . . . " for PLL field 805.

In one embodiment, data in an SM field such as SM field 810, 820, and/or 835 may be configured to be relatively short compared to the data in PLL field 805 and/or User Data field 815. Making SM field 810 relatively short may improve format efficiency. In some cases, timing recovery module 130 may configure the data in SM field 810 to be different than any combination which may be found within a User Data field such as User Data field 815 and/or User Data field 830, etc.

In embodiments that implement DNA sequences with homopolymers, the data in SM field 810 may be configured to be long enough to reduce the likelihood of finding that pattern of data in a User Data field. In some cases, the data in SM field 810 may be encoded to eliminate the possibility of finding the same data pattern in a User Data field.

In embodiments that block the use of DNA sequences with homopolymers, timing recovery module 130 may configure the data in SM field 810 to be long enough to reduce the likelihood of finding that same pattern of data in a User Data field. Similar to sequences with homopolymers, the data in the SM field where no homopolymers are used may be encoded to eliminate the possibility of finding the same data pattern in the User Data field. In some cases, the data in the SM field may be based on a multi-dimensional mapping of binary data to sequences of DNA bases.

In some embodiments, data in SM field 810, 820, and/or 835 may be based at least in part on patterns or sequences prohibited according to multidimensional mapping criteria.

For example, referring to FIGS. 4-7, the sequence "CTCT . . . " may be one pattern or sequence of DNA bases that is prohibited from being used in any portion of the data in a User Data field according to certain conditions of the multidimensional mapping criteria (e.g., when $b_{n-2}$=G, $b_{n-2}$=T, $b_{n-2}$=A, or $b_{n-2}$=C). Accordingly, the sequence "CTCT . . . " may be used for SM field 810 following the sequence "ACAGTGACAGTG . . . " used in PLL field 805.

Upon processing PLL field 805 and detection of SM field 810 by timing recovery module 130, the timing information for the DNA storage system may be assumed to be accurate. In some cases, timing recovery module 130 may track changes in timing using the User Data field 815. In some cases, timing recovery module 130 may perform sampling by freezing the timing information and using a free running clock. It is noted that a DNA storage system with no homopolymers provides an opportunity for timing recovery. Using no homopolymers results in transitions between each DNA base of a sequence, providing timing information that may be utilized for tracking, resulting in high bandwidth timing recovery updates by timing recovery module 130.

In one embodiment, timing recovery module 130 may implement repeatedly placed SM fields in data layout 800 by embedding SMs within a User Data field. The advantage of embedding SM data within a User Data field may be two-fold: (1) providing an updating of the timing information; and (2) providing detection and/or correction of insertion and/or deletion of DNA bases during an associated DNA write process.

With reference to updating the timing information, timing recovery module 130 may detect a second SM relative to a first SM, where the first SM occurs in the sequence of encoded data before the second SM (e.g., the second SM is the next SM after the first SM or one or more other SMs occur between the prior first SM and the subsequent second SM). In one embodiment, timing recovery module 130 may determine a location of the second SM. In some cases, timing recovery module 130 may determine the location of the second SM relative to a number of samples between the second SM and the first SM. In one embodiment, a sample may refer one or more DNA bases in a sequence of DNA bases. In some cases, timing recovery module 130 may compare the determined location of the second SM with a predefined expected location for the second SM. In one embodiment, when timing recovery module 130 determines that the determined location of the second SM is at its predefined expected location (e.g., the second SM is determined to be located an expected number of samples away from the first SM), then timing recovery module 130 may update the phase and frequency offsets accordingly and/or run timing recovery for subsequent User Data fields based at least in part on the resulting updated phase and frequency offsets.

In one embodiment, when timing recovery module 130 determines that the determined location of the second SM is before or ahead its predefined expected location (e.g., detecting less samples than expected between the first SM and the second SM), then timing recovery module 130 may determine that the location of the second SM indicates a deletion. In some cases, the expected location of the second SM may be defined in relation to a predetermined number of samples from the first SM. In one embodiment, the number of deleted DNA bases $N_d$ may be equal to the difference between the detected location of the second SM and the predefined expected location of the second SM. In one example, the expected location of the second SM may be based at least in part on an expectation of there being 10 samples between the second SM and the first SM. Upon determining only 8 samples between the second SM and the first SM, timing recovery module 130 may identify a deletion of 2 samples.

In one embodiment, when timing recovery module 130 determines that the location of the second SM is after its expected predefined location (e.g., detecting more samples than expected between the second SM and the first SM), then timing recovery module 130 may determine that the location of the second SM indicates an insertion.

In some cases, the expected location of the second SM may be defined in relation to a predetermined number of samples from the first SM. In one embodiment, the number of inserted DNA bases $N_i$ may be equal to the difference between the detected location of the second SM and the predefined expected location of the second SM. In one example, the expected location of the second SM may be based at least in part on an expectation of there being 10 samples between the second SM and the first SM. Upon determining 14 samples between the second SM and the first SM, timing recovery module 130 may identify an insertion of 4 samples.

In one embodiment, timing recovery module 130 may identify each possible combination of DNA bases of length $N_d$. In some cases, each identified combination of DNA bases of length $N_d$ may be referred to as potential replacement sequences to be inserted within an associated User Data field. As one example, if $N_d$=2, then timing recovery module 130 may identify AA, AC, AT, AG, CA, CC, CT, CG, TA, TC, TT, TG, GA, GC, GT, and GG as possible combinations of DNA bases of length $N_d$=2. If homopolymers are not allowed, then timing recovery module 130 may remove AA, CC, TT, and GG as possible combinations. Additionally or alternatively, if certain combinations such as CT are not allowed, as one example, then timing recovery module 130 may remove such prohibited combinations from the list of possible combinations, etc.

For each potential replacement sequence, timing recovery module 130 may insert a given potential replacement sequence into an associated User Data. In some cases, timing recovery module 130 may iteratively determine whether the overall coded User Data with a particular potential replacement sequence inserted is a recognized codeword of an associated error correction code predetermined to be associated with the DNA storage system (e.g., low-density parity check (LDPC), Reed-Solomon (RS), etc.). Upon determining the currently tested specific combination is a recognized codeword, then timing recovery module 130 may identify the given potential replacement sequence as the deleted sequence and determine the currently tested specific combination is a successful deletion correction.

In one embodiment, timing recovery module 130 may identify each possible combination of DNA bases of length $N_i$. In some cases, each identified combination of DNA bases of length $N_i$ may be referred to as potential extraction sequences to be extracted from an associated User Data field. For each potential extraction sequence, timing recovery module 130 may extract a given potential extraction sequence from an associated User Data. In some cases, timing recovery module 130 may iteratively determine whether the overall coded User Data with a particular potential extraction sequence removed matches a recognized codeword of an associated error correction code predetermined to be associated with the DNA storage system. Upon determining the currently tested specific combination is a recognized codeword, then timing recovery module 130 may identify the given potential extraction sequence as the inserted sequence and determine the currently tested specific combination is a successful insertion correction.

Figure 9:
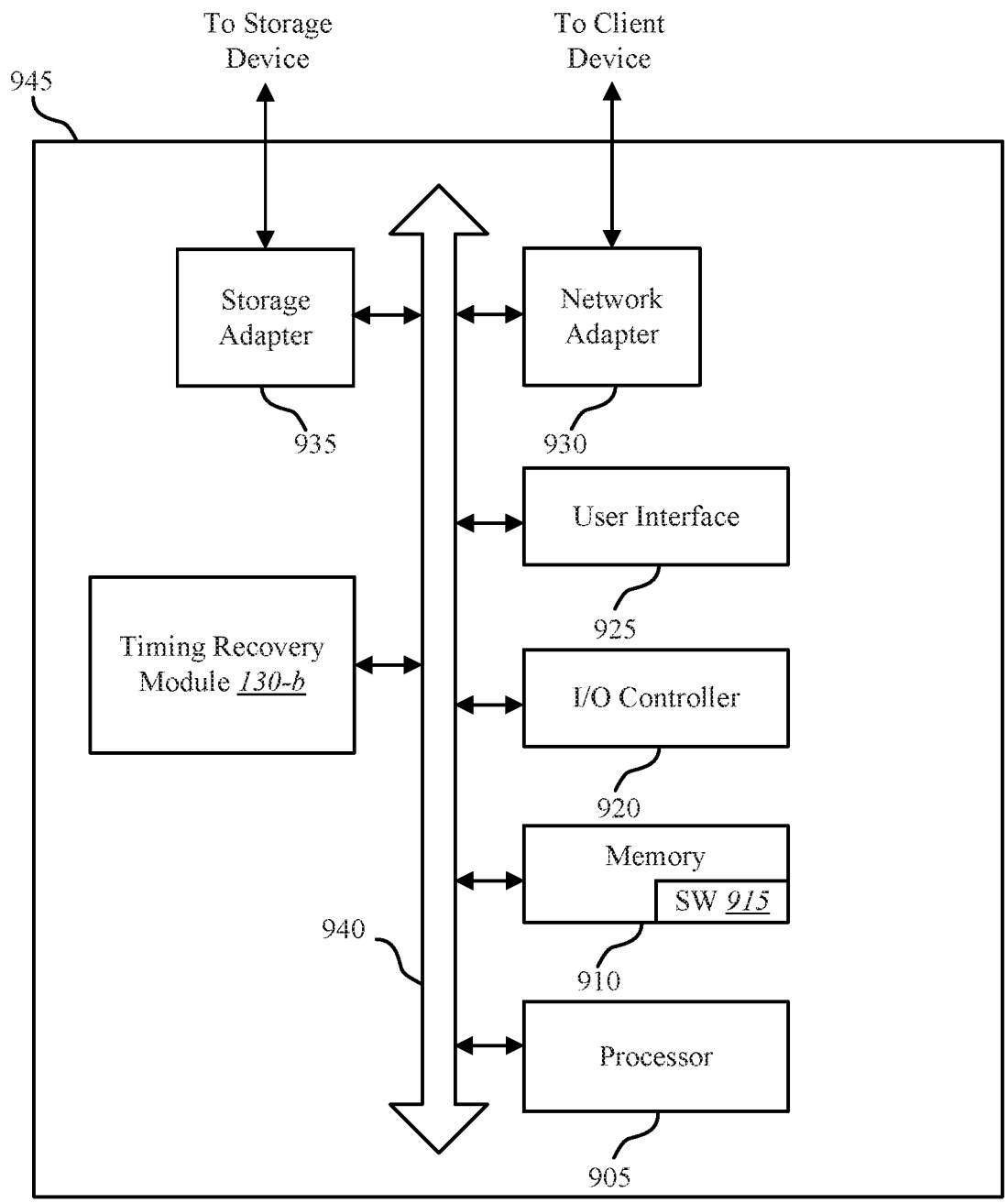
FIG. 9 shows one embodiment of a system in accordance with various aspects of this disclosure.

FIG. 9 shows a system 900 for multi-dimensional mapping of DNA sequences, in accordance with various examples. System 900 may include an apparatus 945, which may be an example of any one of device 105 of FIG. 1.

Apparatus 945 may include components for bi-directional voice and data communications including components for transmitting communications and components for receiving communications. For example, apparatus 945 may communicate bi-directionally with one or more storage devices (e.g., DNA storage devices) and/or client systems. This bi-directional communication may be direct (apparatus 945 communicating directly with a storage system, for example) and/or indirect (apparatus 945 communicating indirectly with a storage device or client device through a server, for example).

Apparatus 945 may also include a processor module 905, and memory 910 (including software/firmware code (SW) 915), an input/output controller module 920, a user interface module 925, a network adapter 930, and a storage adapter 935. Apparatus 945 may include one or more processors. The software/firmware code 915 may be one example of a software application executing on apparatus 945. The network adapter 930 may communicate bi-directionally, via one or more wired links and/or wireless links, with one or more networks and/or client devices. In some embodiments, network adapter 930 may provide a direct connection to a client device via a direct network link to the Internet via a POP (point of presence). In some embodiments, network adapter 930 of apparatus 945 may provide a connection using wireless techniques, including digital cellular telephone connection, Cellular Digital Packet Data (CDPD) connection, digital satellite data connection, and/or another connection. The apparatus 945 may include timing recovery module 130-b, which may perform the functions described above for the timing recovery module 130 of FIGS. 1 and/or 2.

The signals associated with system 900 may include wireless communication signals such as radio frequency, electromagnetics, local area network (LAN), wide area network (WAN), virtual private network (VPN), wireless network (using 802.11, for example), cellular network (using 3G and/or LTE, for example), and/or other signals. The network adapter 930 may enable one or more of WWAN (GSM, CDMA, and WCDMA), WLAN (including BLUETOOTH® and Wi-Fi), WMAN (WiMAX) for mobile communications, antennas for Wireless Personal Area Network (WPAN) applications (including RFID and UWB), or any combination thereof.

One or more buses 940 may allow data communication between one or more elements of apparatus 945 such as processor module 905, memory 910, I/O controller module 920, user interface module 925, network adapter 930, and storage adapter 935, or any combination thereof. One or more of the components of the apparatus 945, individually or collectively, may be implemented using one or more application-specific integrated circuits (ASICs) adapted to perform some or all of the applicable functions in hardware. Alternatively, the functions may be performed by one or more other processing units (or cores), on one or more integrated circuits. In other examples, other types of integrated circuits may be used such as Structured/Platform ASICs, Field Programmable Gate Arrays (FPGAs), and other Semi-Custom ICs, which may be programmed in any manner known in the art. The functions of each module may also be implemented, in whole or in part, with instructions embodied in memory formatted to be executed by one or more general and/or application-specific processors.

The memory 910 may include random access memory (RAM), read only memory (ROM), flash memory, and/or other types. The memory 910 may store computer-readable, computer-executable software/firmware code 915 including instructions that, when executed, cause the processor module 905 to perform various functions described in this disclosure. Alternatively, the software/firmware code 915 may not be directly executable by the processor module 905 but may cause a computer (when compiled and executed, for example) to perform functions described herein. Alternatively, the computer-readable, computer-executable software/firmware code 915 may not be directly executable by the processor module 905, but may be configured to cause a computer, when compiled and executed, to perform functions described herein. The processor module 905 may include an intelligent hardware device, for example, a central processing unit (CPU), a microcontroller, an application-specific integrated circuit (ASIC), field programmable gate array (FPGA), or any combination thereof.

In some embodiments, the memory 910 may contain, among other things, the Basic Input-Output system (BIOS) which may control basic hardware and/or software operation such as the interaction with peripheral components or devices. For example, at least a portion of the timing recovery module 130-b to implement the present systems and methods may be stored within the system memory 910. Applications resident with system 900 are generally stored on and accessed via a non-transitory computer readable medium, such as a hard disk drive or other storage medium. Additionally, applications can be in the form of electronic signals modulated in accordance with the application and data communication technology when accessed via a network interface such as network adapter 930.

Many other devices and/or subsystems may be connected to and/or included as one or more elements of system 900 (for example, a personal computing device, mobile computing device, smart phone, server, internet-connected device, cell radio module, or any combination thereof). In some embodiments, all of the elements shown in FIG. 9 need not be present to practice the present systems and methods. The devices and subsystems can be interconnected in different ways from that shown in FIG. 9. In some embodiments, an aspect of some operation of a system, such as that shown in FIG. 9, may be readily known in the art and are not discussed in detail in this application. Code to implement the present disclosure can be stored in a non-transitory computer-readable medium such as one or more of system memory 910 or other memory. The operating system provided on I/O controller module 920 may be a mobile device operation system, a desktop/laptop operating system, a server operating system, or another known operating system.

The I/O controller module 920 may operate in conjunction with network adapter 930 and/or storage adapter 935. The network adapter 930 may enable apparatus 945 with the ability to communicate with client devices such as device 105 of FIG. 1, and/or other devices over a communication network. Network adapter 930 may provide wired and/or wireless network connections. In some cases, network adapter 930 may include an Ethernet adapter or Fibre Channel adapter. Storage adapter 935 may enable apparatus 945 to access one or more data storage devices such as storage device 110. The one or more data storage devices may include two or more data tiers each. The storage adapter 935 may include one or more of an Ethernet adapter, a Fibre Channel adapter, Fibre Channel Protocol (FCP) adapter, a SCSI adapter, and iSCSI protocol adapter.

Figure 10:
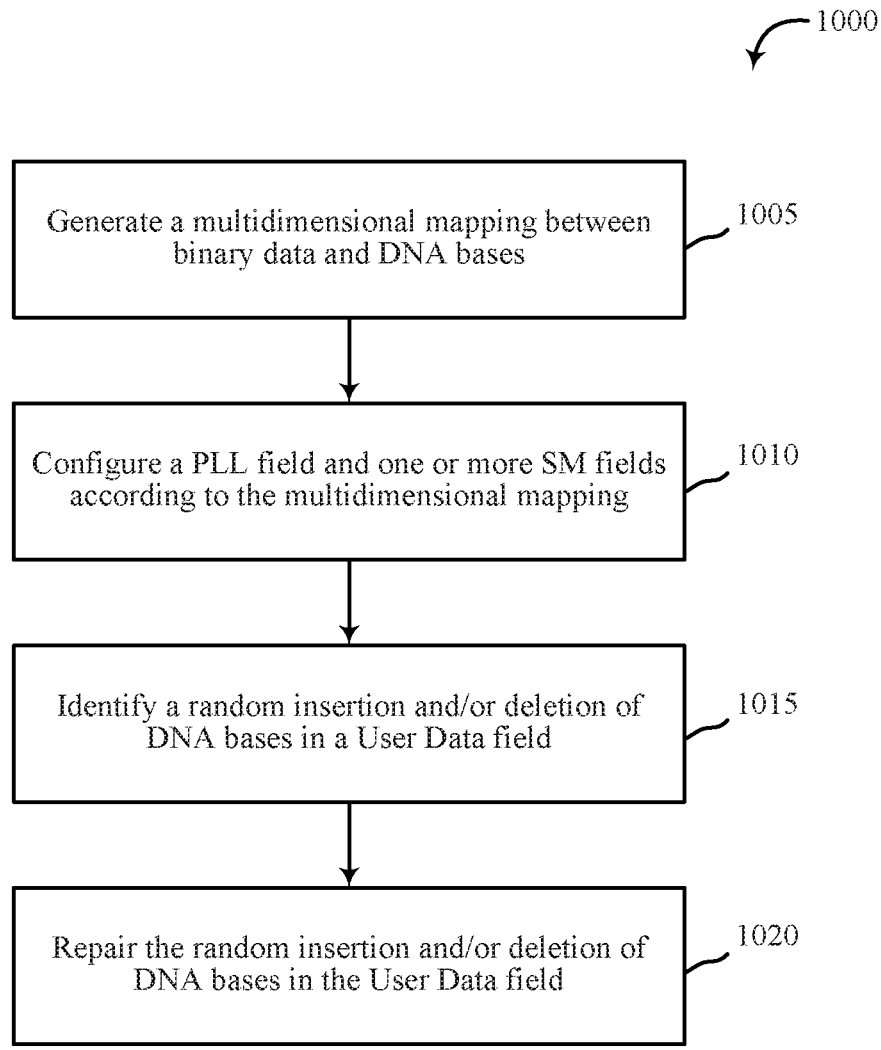
FIG. 10 is a flow chart illustrating an example of a method in accordance with various aspects of this disclosure.

FIG. 10 is a flow chart illustrating an example of a method 1000 for multi-dimensional mapping of DNA sequences, in accordance with various aspects of the present disclosure. One or more aspects of the method 1000 may be implemented in conjunction with device 105 of FIG. 1, apparatus 945 of FIG. 9, and/or timing recovery module 130 depicted in FIGS. 1, 2 and/or 9. In some examples, a backend server, computing device, and/or storage device may execute one or more sets of codes to control the functional elements of the backend server, computing device, and/or storage device to perform one or more of the functions described below. Additionally or alternatively, the backend server, computing device, and/or storage device may perform one or more of the functions described below using special-purpose hardware.

At block 1005, method 1000 may include generating a multidimensional mapping between binary data and DNA bases. At block 1010, method 1000 may include configuring a PLL field and one or more SM fields according to the multidimensional mapping. At block 1015, method 1000 may include identifying a random insertion and/or deletion of DNA bases in a User Data field. At block 1020, method 1000 may include repairing the random insertion and/or deletion of DNA bases in the User Data field.

The operation(s) at block 1005-1020 may be performed using the timing recovery module 130 described with reference to FIGS. 1, 2, and 9, and/or another module described herein. Thus, the method 1000 may provide for multi-dimensional mapping of binary data DNA sequences. It should be noted that the method 1000 is just one implementation and that the operations of the method 1000 may be rearranged, omitted, and/or otherwise modified such that other implementations are possible and contemplated.

Figure 11:
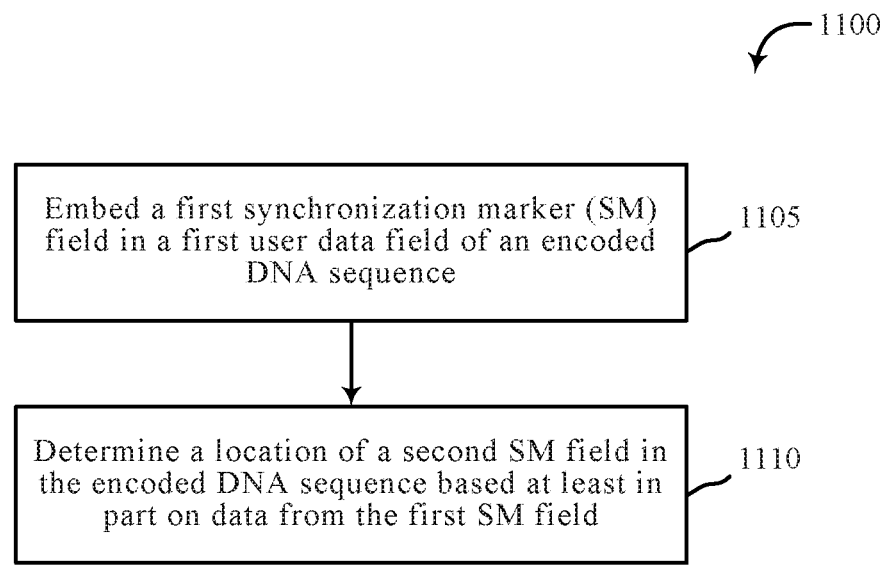
FIG. 11 is a flow chart illustrating an example of a method in accordance with various aspects of this disclosure.

FIG. 11 is a flow chart illustrating an example of a method 1100 for multi-dimensional mapping of DNA sequences, in accordance with various aspects of the present disclosure. One or more aspects of the method 1100 may be implemented in conjunction with device 105 of FIG. 1, apparatus 945 of FIG. 9, and/or timing recovery module 130 depicted in FIGS. 1, 2 and/or 9. In some examples, a backend server, computing device, and/or storage device may execute one or more sets of codes to control the functional elements of the backend server, computing device, and/or storage device to perform one or more of the functions described below. Additionally or alternatively, the backend server, computing device, and/or storage device may perform one or more of the functions described below using special-purpose hardware.

At block 1105, method 1100 may include embedding a first synchronization mark (SM) field in a first user data field of an encoded DNA sequence. At block 1110, method 1100 may include determining a location of a second SM field in the encoded DNA sequence based at least in part on data from the first SM field. In some cases, the second SM field may be subsequent to the first SM field in the encoded DNA sequence. In some examples, the encoded DNA sequence may include at least one of each of a synchronization mark (SM) field, a phase locked loop (PLL) field, and a user data field. In some embodiments, the method for timing recovery in DNA storage systems and the method for recovering timing information from DNA encoded data are the same method or elements of the same method The operation(s) at block 1105 and 1110 may be performed using the timing recovery module 130 described with reference to FIGS. 1, 2, and 9, and/or another module described herein. Thus, the method 1100 may provide for multi-dimensional mapping of binary data DNA sequences. It should be noted that the method 1100 is just one implementation and that the operations of the method 1100 may be rearranged, omitted, and/or otherwise modified such that other implementations are possible and contemplated.

In some examples, aspects from two or more of methods 1000 and 1100 may be combined and/or separated. It should be noted that methods 1000 and 1100 are just example implementations, and that the operations of methods 1000 and 1100 may be rearranged or otherwise modified such that other implementations are possible.

The detailed description set forth above in connection with the appended drawings describes examples and does not represent the only instances that may be implemented or that are within the scope of the claims. The terms "example" and "exemplary," when used in this description, mean "serving as an example, instance, or illustration," and not "preferred" or "advantageous over other examples." The detailed description includes specific details for the purpose of providing an understanding of the described techniques. These techniques, however, may be practiced without these specific details. In some instances, known structures and apparatuses are shown in block diagram form in order to avoid obscuring the concepts of the described examples.

Information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and components described in connection with this disclosure may be implemented or performed with a general-purpose processor, a digital signal processor (DSP), an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, and/or state machine. A processor may also be implemented as a combination of computing devices, for example, a combination of a DSP and a microprocessor, multiple microprocessors, one or more microprocessors in conjunction with a DSP core, and/or any combination thereof.

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope and spirit of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations.

As used herein, including in the claims, the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination. Also, as used herein, including in the claims, "or" as used in a list of items (for example, a list of items prefaced by a phrase such as "at least one of" or "one or more of") indicates a disjunctive list such that, for example, a list of "at least one of A, B, or C" means A or B or C or AB or AC or BC or ABC, or A and B and C.

In addition, any disclosure of components contained within other components or separate from other components should be considered exemplary because multiple other architectures may potentially be implemented to achieve the same functionality, including incorporating all, most, and/or some elements as part of one or more unitary structures and/or separate structures.

Computer-readable media includes both computer storage media and communication media including any medium that facilitates transfer of a computer program from one place to another. A storage medium may be any available medium that can be accessed by a general purpose or special purpose computer. By way of example, and not limitation, computer-readable media can comprise RAM, ROM, EEPROM, flash memory, CD-ROM, DVD, or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, or any combination thereof, then the coaxial cable, fiber optic cable, twisted pair, DSL, or wireless technologies such as infrared, radio, and/or microwave are included in the definition of medium. Disk and disc, as used herein, include any combination of compact disc (CD), laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The previous description of the disclosure is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not to be limited to the examples and designs described herein but is to be accorded the broadest scope consistent with the principles and novel features disclosed.

This disclosure may specifically apply to security system applications. This disclosure may specifically apply to storage system applications. In some embodiments, the concepts, the technical descriptions, the features, the methods, the ideas, and/or the descriptions may specifically apply to storage and/or data security system applications. Distinct advantages of such systems for these specific applications are apparent from this disclosure.

The process parameters, actions, and steps described and/or illustrated in this disclosure are given by way of example only and can be varied as desired. For example, while the steps illustrated and/or described may be shown or discussed in a particular order, these steps do not necessarily need to be performed in the order illustrated or discussed.

The various exemplary methods described and/or illustrated here may also omit one or more of the steps described or illustrated here or include additional steps in addition to those disclosed.

Furthermore, while various embodiments have been described and/or illustrated here in the context of fully functional computing systems, one or more of these exemplary embodiments may be distributed as a program product in a variety of forms, regardless of the particular type of computer-readable media used to actually carry out the distribution. The embodiments disclosed herein may also be implemented using software modules that perform certain tasks. These software modules may include script, batch, or other executable files that may be stored on a computer-readable storage medium or in a computing system. In some embodiments, these software modules may permit and/or instruct a computing system to perform one or more of the exemplary embodiments disclosed here.

This description, for purposes of explanation, has been described with reference to specific embodiments. The illustrative discussions above, however, are not intended to be exhaustive or limit the present systems and methods to the precise forms discussed. Many modifications and variations are possible in view of the above teachings. The embodiments were chosen and described in order to explain the principles of the present systems and methods and their practical applications, to enable others skilled in the art to utilize the present systems, apparatus, and methods and various embodiments with various modifications as may be suited to the particular use contemplated.

user data field of an encoded DNA sequence and determine a location of a second SM field in the encoded DNA sequence based at least in part on data from the first SM field, identify an insertion of one or more DNA bases from the encoded DNA sequence upon determining that the determined location of the second SM field occurs in the encoded DNA sequence after an expected location of the second SM field and remove the one or more inserted DNA bases from the encoded DNA sequence, wherein the second SM field is subsequent to the first SM field in the encoded DNA sequence, the encoded DNA sequence comprising at least one SM field and at least one user data field.

2. The DNA timing recovery system of claim 1, wherein the one or more processors are configured to:
compare the expected location of the second SM field to the determined location of the second SM field.

3. The DNA timing recovery system of claim 2, wherein the one or more processors are configured to:
upon determining that the determined location of the second SM field occurs in the encoded DNA sequence before the expected location of the second SM field, identify a deletion of one or more DNA bases from the encoded DNA sequence and replace the one or more deleted DNA bases in the encoded DNA sequence.

4. The DNA timing recovery system of claim 2, wherein the one or more processors are configured to:
extract timing information from the encoded DNA sequence upon determining that the determined loca-

---

---

What is claimed is:

1. A deoxyribonucleic acid (DNA) timing recovery system for recovering timing information from DNA-encoded data, the DNA timing recovery system comprising:
one or more processors configured to process instructions stored in one or more computer-readable memories to embed a first synchronization mark (SM) field in a first tion of the second SM field matches the expected location of the second SM field.

5. The DNA timing recovery system of claim 4, wherein the timing information includes at least one of a phase and a frequency, wherein extracting the timing information includes at least one of applying a phase offset to the phase, applying a frequency offset to the frequency, updating a phase offset, updating a frequency offset, running timing recovery for a second user data field subsequent to running timing recovery for the first user data field based at least in part on the updated phase offset or the updated frequency offset or both, applying the updated phase offset to the phase, applying the updated frequency offset to the frequency, or any combination thereof.

6. The DNA timing recovery system of claim 1, wherein the SM field includes two different DNA bases repeated in a sequence of DNA bases, the two different DNA bases including at least one of GT, GC, GA, TG, TC, TA, CG, CT, CA, AG, AT, or AC, G being a guanine DNA base, T being a thymine DNA base, C being a cytosine DNA base, and A being an adenine DNA base.

7. The DNA timing recovery system of claim 1, wherein the encoded DNA sequence includes at least two different DNA bases repeated one or more times in a sequence of DNA bases, the at least two different DNA bases including at least one of AG, AAGG, or AAAGGG when homopolymers are allowed, or at least one of ACGT, ATGC, and ACAGTG when homopolymers are not allowed.

8. The DNA timing recovery system of claim 1, wherein the SM field is configured to include at least one less DNA base than the user data field.

9. The DNA timing recovery system of claim 1, wherein no two adjacent DNA bases that occur in the SM field occur adjacently in the user data field.

10. A method for recovering timing information from DNA-encoded data comprising:
embedding a first synchronization mark (SM) field in a first user data field of an encoded DNA sequence;
determining a location of a second SM field in the encoded DNA sequence based at least in part on data from the first SM field;
identifying an insertion of one or more DNA bases from the encoded DNA sequence upon determining that the determined location of the second SM field occurs in the encoded DNA sequence after an expected location of the second SM field; and
removing the one or more inserted DNA bases from the encoded DNA sequence,
wherein the second SM field is subsequent to the first SM field in the encoded DNA sequence, the encoded DNA sequence comprising at least one SM field and at least one user data field.

11. The method of claim 10, comprising:
comparing the expected location of the second SM field to the determined location of the second SM field.

12. The method of claim 11, comprising:
upon determining that the determined location occurs in the encoded DNA sequence before the expected location identifying a deletion of one or more DNA bases from the encoded DNA sequence and replacing the one or more deleted DNA bases in the encoded DNA sequence.

13. The method of claim 11, comprising: extracting timing information from the encoded DNA sequence upon determining that the determined location of the second SM field matches the expected location of the second SM field.

14. The method of claim 13, wherein the timing information includes at least one of a phase and a frequency, wherein extracting the timing information includes at least one of applying a phase offset to the phase, applying a frequency offset to the frequency, updating a phase offset, updating a frequency offset, running timing recovery for a second user data field subsequent to running timing recovery for the first user data field based at least in part on the updated phase offset or the updated frequency offset or both, applying the updated phase offset to the phase, applying the updated frequency offset to the frequency, or any combination thereof.

15. The method of claim 10, wherein the SM field includes two different DNA bases repeated in a sequence of DNA bases, the two different DNA bases including at least one of GT, GC, GA, TG, TC, TA, CG, CT, CA, AG, AT, or AC, G being a guanine DNA base, T being a thymine DNA base, C being a cytosine DNA base, and A being an adenine DNA base.

16. The method of claim 10, wherein the encoded DNA sequence includes two or more DNA bases repeated two or more times in a sequence of DNA bases, the two or more repeated DNA bases including at least one of AG, AAGG, or AAAGGG when homopolymers are allowed, or at least one of ACGT, ATGC, and ACAGTG when homopolymers are not allowed.

17. A computer-program product for recovering timing information from DNA-encoded data, the computer-program product comprising a non-transitory computer-readable medium storing instructions thereon, the instructions being executable by one or more processors to perform the steps of:
embedding a first synchronization mark (SM) field in a first user data field of an encoded DNA sequence;
determining a location of a second SM field in the encoded DNA sequence based at least in part on data from the first SM field, the second SM field being subsequent to the first SM field in the encoded DNA sequence;
identifying an insertion of one or more DNA bases from the encoded DNA sequence upon determining that the determined location of the second SM field occurs in the encoded DNA sequence after an expected location of the second SM field; and
removing the one or more inserted DNA bases from the encoded DNA sequence,
wherein the encoded DNA sequence comprises at least one SM field and at least one user data field, the SM field being configured to include at least one less DNA base than the user data field.

18. The computer-program product of claim 17, wherein the instructions are configured to cause the one or more processors to perform the steps of:
comparing the expected location of the second SM field to the determined location of the second SM field.

* * * * *